United States Patent [19]

Angelucci et al.

[11] Patent Number: 4,749,693

[45] Date of Patent: Jun. 7, 1988

[54] NITRO ANTHRACYCLINES, PROCESS FOR THEIR PREPARATION AND USE THEREOF

[75] Inventors: Francesco Angelucci, Milan; Mauro Gigli, Merano; Sergio Penco, Milan; Fernando Giuliani, Cassina de Pecchi, all of Italy

[73] Assignee: Farmitalia Carlo Erba S.p.A., Milan, Italy

[21] Appl. No.: 912,070

[22] Filed: Sep. 26, 1986

[30] Foreign Application Priority Data

Nov. 19, 1985 [GB] United Kingdom ................ 8528440

[51] Int. Cl.[4] .................... A61K 31/70; C07H 15/24
[52] U.S. Cl. ...................................... 514/34; 536/6.4; 260/365
[58] Field of Search .................. 536/6.4; 514/34; 260/365

[56] References Cited

U.S. PATENT DOCUMENTS

| | | | |
|---|---|---|---|
| 3,803,124 | 4/1974 | Arcamone et al. | 536/6.4 |
| 4,348,388 | 9/1982 | Garland et al. | 536/6.4 |
| 4,465,671 | 8/1984 | Angelucci et al. | 536/6.4 |
| 4,521,592 | 6/1985 | Dahmer et al. | 536/4.1 |
| 4,563,444 | 1/1986 | Angelucci et al. | 514/34 |

OTHER PUBLICATIONS

March, *Advanced Organic Chemistry: Reactions, Mechanisms, and Structure*, 1968, p. 344.

Johnson et al., *Cancer Treatment Reviews* (1975) 2, pp. 1–31.

Cram et al, *Organic Chemistry*, 2nd Ed., published by McGraw Hill Book Company, p. 76, 1964.

Burger's Medicinal Chemistry, Fourth Edition, Part II, Wiley, 1979, pp. 238–241, 595–598, 635–636.

Physician's Desk Reference, 41st Edition, 1987, pp. 208, 209 and 561.

Kirk-Othmer, Encyclopedia of Chemical Technology, Third Ed., vol. 5, Wiley, 1979, pp. 476–479.

Webster's Third New International Dictionary, Unabridged, G. and C Merriam Company, 1976, p. 85.

*Primary Examiner*—J. R. Brown
*Assistant Examiner*—Elli Peselev
*Attorney, Agent, or Firm*—Oblon, Fisher, Spivak, McClelland & Maier

[57] ABSTRACT

Anthracycline glycosides of the general formula (A'):

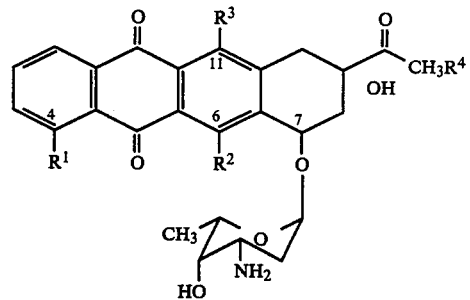

wherein $R_1$ represents a hydrogen atom, a hydroxy group or a methoxy group; one of $R_2$ and $R_3$ represents a hydroxy group and the other of $R_2$ and $R_3$ represents a nitro group; and $R_4$ represents a hydrogen atom or a hydroxy group; and their pharmaceutically acceptable salts; have anti-tumor activity.

15 Claims, No Drawings

NITRO ANTHRACYCLINES, PROCESS FOR THEIR PREPARATION AND USE THEREOF

DESCRIPTION

The invention relates to new anthracycline glycosides having antitumor activity, to methods for their preparation and to pharmaceutical compositions containing them.

The invention provides anthracycline glycosides of the general formula (A'):

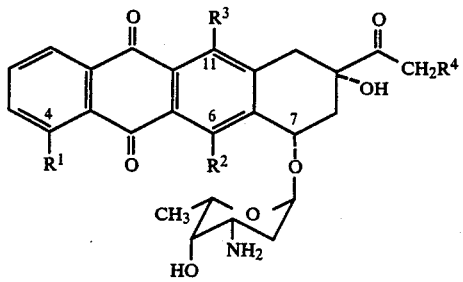

wherein $R_1$ represents a hydrogen atom, a hydroxy group or a methoxy group; one of $R_2$ and $R_3$ represents a hydroxy group and the other of $R_2$ and $R_3$ represents a nitro group; and $R_4$ represents a hydrogen atom or a hydroxy group; and pharmaceutically acceptable salts thereof. The invention also provides compounds, useful in the preparation of the compounds of formula (A'), of general formula (A'''):

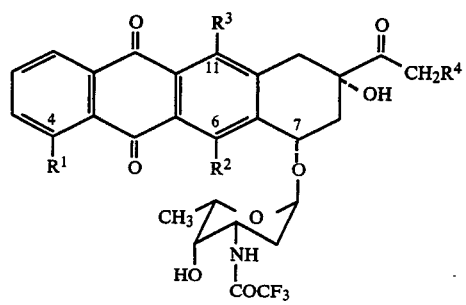

wherein $R^1$, $R^2$, $R^3$ and $R^4$ are as defined as above.

More precisely, the compounds of the invention are characterised by the following patterns of substitution:

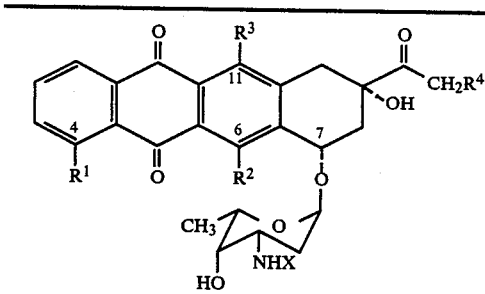

| Structure | Substitution |
|---|---|
| I | $R^1 = R^4 = H$; $R^2 = NO_2$; $R^3 = OH$; $X = COCF_3$ |
| II | $R^1 = R^4 = H$; $R^2 = NO_2$; $R^3 = OH$; $X = H$ |
| III | $R^1 = H$; $R^2 = NO_2$; $R^3 = R^4 = OH$; $X = H$ |
| IV | $R^1 = R^3 = OH$; $R^2 = NO_2$; $R^4 = H$; $X = COCF_3$ |
| V | $R^1 = R^3 = OH$; $R^2 = NO_2$; $R^4 = H$; $X = H$ |

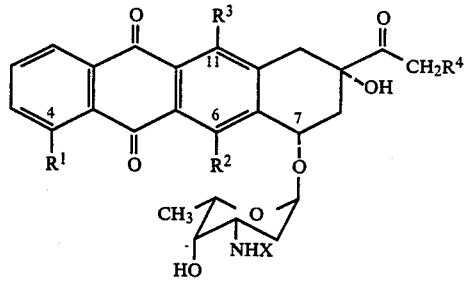

| Structure | Substitution |
|---|---|
| VI | $R^1 = R^3 = R^4 = OH$; $R^2 = NO_2$; $X = H$ |
| VII | $R^1 = OCH_3$; $R^2 = NO_2$; $R^3 = OH$; $R^4 = H$; $X = COCF_3$ |
| VIII | $R^1 = OCH_3$; $R^2 = NO_2$; $R^3 = OH$; $R^4 = H$; $X = H$ |
| IX | $R^1 = OCH_3$; $R^2 = NO_2$; $R^3 = R^4 = OH$; $X = H$ |
| X | $R^1 = R^4 = H$; $R^2 = OH$; $R^3 = NO_2$ $X = COCF_3$ |
| XI | $R^1 = R^4 = H$; $R^2 = OH$; $R^3 = NO_2$ $X = H$ |
| XII | $R^1 = H$; $R^2 = R^4 = OH$; $R^3 = NO_2$; $X = H$ |
| XIII | $R^1 = R^2 = OH$; $R^3 = NO_2$; $R^4 = H$ $X^1 = COCF_3$ |
| XIV | $R^1 = R^2 = OH$; $R^3 = NO_2$; $R^4 = H$; $X = H$ |
| XV | $R^1 = R^2 = R^4 = OH$; $R^3 = NO_2$; $X = H$ |
| XVI | $R^1 = OCH_3$; $R^2 = OH$; $R^3 = NO_2$; $R^4 = H$; $X = COCF_3$ |
| XVII | $R^1 = OCH_3$; $R^2 = OH$; $R^3 = NO_2$; $R^4 = H$; $X = H$ |
| XVIII | $R^1 = OCH_3$; $R^2 = R^4 = OH$; $R^3 = NO_2$; $X = H$ |

Preferred compounds are the hydrochloride salts of the compounds of formula (A').

The anthracycline glycocisides of formula (A') and their pharmaceutically acceptable salts are prepared according to the present invention by condensing an aglycone of the general formula (B):

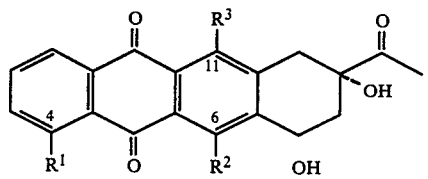

wherein $R^1$, $R^2$ and $R^3$ are as defined above, with 1-chloro-N,O-di(trifluoroacetyl)daunosamine of formula (C):

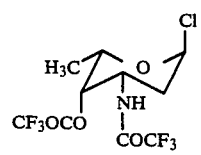

so as to form a diastereomeric mixture of 7(S), 9(S) and 7(R), 9(R) anthracycline glycosides of formula (A'')

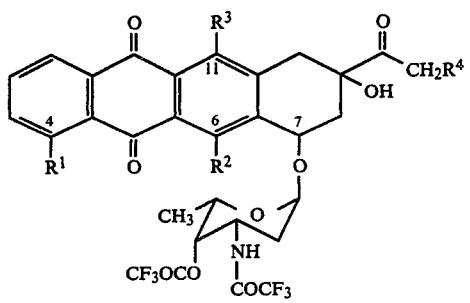

wherein $R^1$, $R^2$ and $R^3$ are as defined above; removing the O-trifluoroacetyl group; separating the 7(S), 9(S) anthracycline glycoside from the 7(R), 9(R) anthracycline glycoside; removing the N-trifluoroacetyl protecting group from the 7(S), 9(S) anthracycline glycoside so as to obtain a compound of formula (A′) in which $R^4$ is hydrogen; if desired, converting the said compound of formula (A′) into a pharmaceutically acceptable salt thereof; if desired, brominating the said compound of formula (A′) or pharmaceutically acceptable salt thereof and hydrolysing the 14-bromo derivative thus obtained so as to form a compound of formula (A′) in which $R^4$ is hydroxy; and, if desired, converting the compound of formula (A′) in which $R^4$ is hydroxy into a pharmaceutically acceptable salt thereof.

Thus after removing, typically by hydrolysis, the trifluoroacetyl protecting groups of the sugar moiety, the daunorubicin analog glycosides are obtained. The doxorubicin analogs are prepared from the corresponding daunorubicin analogs via 14-bromo derivatives in accordance with the method described in U.S. Pat. No. 3,803,124.

The process for preparing the new anthracyclines, disclosed herein, is based on the direct nitration of ring B of anthracycline intermediates characterized by having an hydroxyl group in the para-position to the reaction center. The introduction of the nitro group is performed generally by using trifluoroacetic anhydride/ammonium nitrate reagent. The reaction must be carried out in absence of oxygen and moisture otherwise the reagents operate as oxidant allowing the introduction of an aromatic hydroxyl group instead of the nitro group, and then the corresponding oxidation products (see J. V. Crivello, J. Org. Chem. 46, 3056, 1981). The resulting compound is an aglycone of formula (B). The aglycones form part of the invention.

The general synthetic route followed for preparing the 6-nitro and 11-nitro anthracyclines of formula (B) are reported in Schemes I and II respectively below.

Our approach is based on the use of, as starting material, for the 6-nitro anthracyclinones, (±)4-dimethoxy-6-deoxydaunomycinone 1 (R=H), (W. Germ. Off. No. 3219380) and (±)6-deoxydaunomycinone 1 (R=OCH₃), (UK Specification No. 2142022A) and, for the 11-nitro anthracyclinones, (±)4-demethoxy-11-deoxydaunomycinone 7 (R=H), (W. Germ. Off. No. 3219380) and 11-deoxydaunomycinone 7 (R=OCH₃) obtained by acid hydrolysis of the natural antibiotic (Arcamone et al. JACS, 102, 1462, 1980).

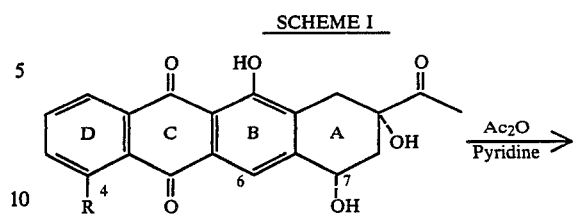

SCHEME I

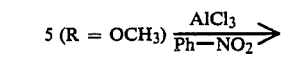

wherein R = H, OCH₃

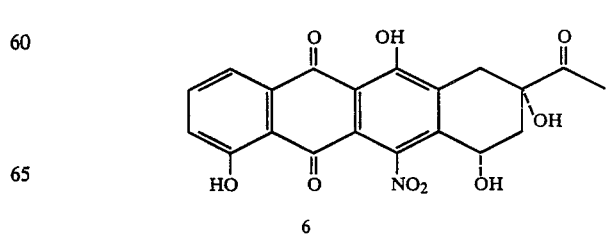

SCHEME II

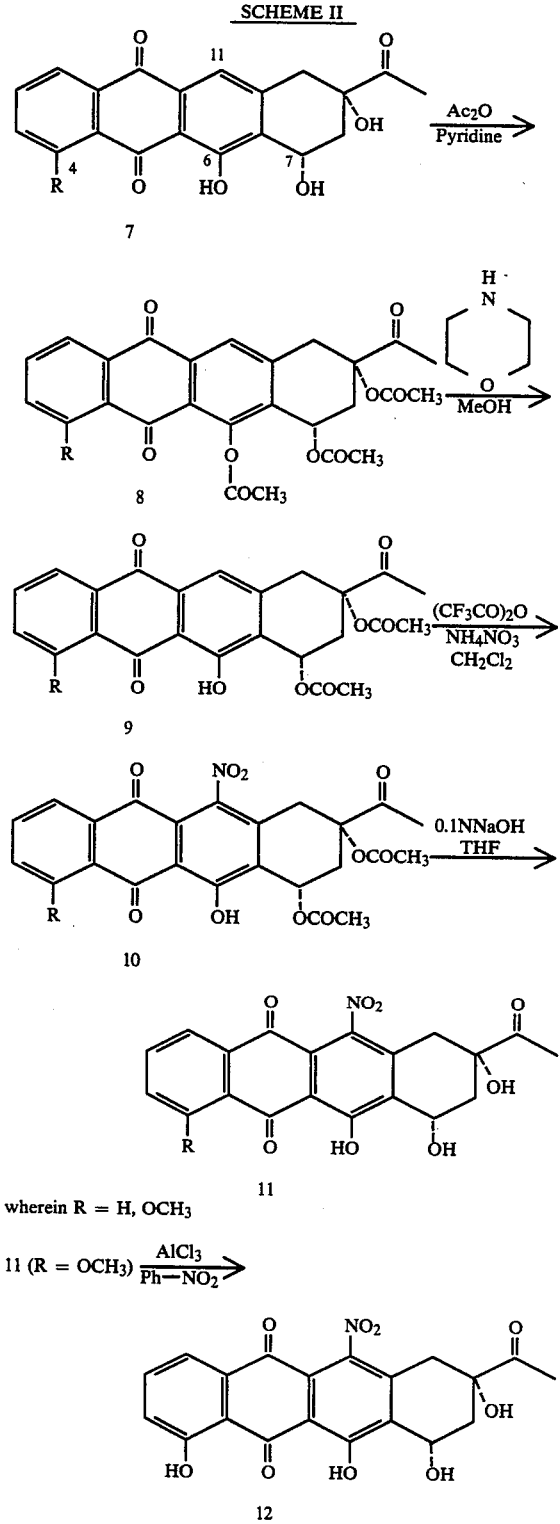

wherein R = H, OCH$_3$

In order to avoid the nitrate formation of the C—7—OH and C-9—OH these hydroxyl groups are protected, e.g. as acetates. This can be achieved by treatment of 1 and 7 with acetic anhydride in the presence of pyridine at from 85° to 90° C. to acylate all the free hydroxy groups to give 2 and 8, respectively, followed by selective hydrolysis of these aromatic triacetates by using morpholine as base so obtaining 3 and 9 in nearly quantitative yields. Preferably 1N morpholine is used in methanol at 40° C. for 5 hours.

Nitration is typically performed with excess of trifluoroacetic anhydride/ammonium nitrate in methylene chloride. The nitration can be performed at room temperature under a nitrogen atmosphere and with vigorous stirring. This can afford the corresponding nitro dervatives 4 and 10, in yields of 70% for example.

Finally mild alkaline hydrolysis with 0.1N NaOH in tetrahydrofurane at room temperature and under a nitrogen atmosphere can give the aglycones:

(±)4-demethoxy-6-deoxy-6-nitrodaunomycinone 5 (R=H)

(±)6-deoxy-6-nitrodaunomycinone 5 (R=OCH$_3$)

(±)4-demethoxy-11-deoxy-11-nitrodaunomycinone 11 (R=H)

11-deoxy-11-nitrodaunomycinone 11 (R=OCH$_3$)

The aglycones can optionally be purified by chromatography on silica gel. Mild dealkylation with AlCl$_3$·Ph—NO$_2$ of 5 and 11 for R=OCH$_3$ can afford the corresponding:

(±)6-deoxy-6-nitrocarminomycinone 6

11-deoxy-11-nitrocarminomycinone 12

Thus, the aglycones of formula (B) may be prepared according to the invention by selectively protecting the C-7 and C-9 hydroxy groups of (±)4-demethoxy-6-deoxydaunomycinone, (±)6-deoxydaunomycinone, 4-demethoxy-11-deoxydaunomycinone or 11-deoxydaunomycinone; nitrating the ring B of the compound thus formed at the para-position with respect of hydroxy substituent on ring B; removing the C-7 and C-9 hydroxy protecting groups so as to obtain an aglycone of formula (B) in which R$^1$ is hydrogen or methoxy; and, if desired, converting the aglycone of formula (B) in which R$^1$ is methoxy into an aglycone of formula (B) in which R$^1$ is hydroxy.

The corresponding glycosides are prepared by coupling 5(R=H, OCH$_3$), 6, 11(R=H, OCH$_3$) and 12 with the 1-chloro-N,O— di(trifluoroacetyl)daunosamine, preferably in the presence of silver trifluoromethanesulfonate in anhydrous methylene dichloride under a nitrogen atmosphere. This gives, after hydrolysis of the O-trifluoroacetyl group by treatment with methanol, the α-glycosides I, IV, VII, X, XIII, XVI as a mixture of diastereoisomers 7(S):9(S) and 7(R):9(R).

After separation e.g. by chromatography on silica gel, the 7(S):9(S) glycosides are subjected to mild alkaline hydrolysis, in order to remove the N-trifluroacetyl group, so giving the corresponding daunorubicin analogs II, V, VIII XI, XIV, XVII. These may be isolated as their hydrochlorides by treatment with hydrogen chloride in methanol and, if desired, converted to the corresponding doxorubicin analogs III, VI, IX, XII, XV, XVIII, via 14-bromination and treatment with aqueous sodium formate in accordance with the method described in U.S. Pat. No. 3,803,124. The doxorubicin analogs can be isolated as their hydrochlorides as above.

The invention is illustrated by the following Examples.

EXAMPLE 1

(±) 4-demethoxy-6-deoxy-6-nitrodaunomycinone 5 (R=H)

(a) Preparation of intermediate 2 (R=H)

Product 1 (1.7 g, 4.8 mM) was heated at 90° C. under stirring with acetic anhydride (25 ml) and pyridine (25 ml). After 2 hr the reaction mixture was poured in ice/water and left to stand for 30' under stirring. The solid material was filtered, washed with $H_2O$ and crystallized from MeOH to give 2 (2.19 g, yield 94%). m.p. 225°–226° C.

IR (KBr): 1770 (aromatic ester), 1740 (aliphatic ester), 1720 (aliphatic ketone), 1675 (aromatic ketone), 1590 (Ar) $cm^{-1}$.

UV (MeOH) λmax: 210, 258, 334 nm.

FD-MS: m/z 478 (100, $M^{+\cdot}$).

PMR (200 MHz, $CDCl_3$), inter alia: δ 2.11, 2.01 (s, 6H, $OCOCH_3$), 2.22 (s, 3H, $COCH_3$), 2.52 (s, 3H, Ar—$OCOCH_3$), 2.4–3.3 (m, 4H), 6.17 (broad, 1H, 7-H), 7.7–8.25 (m, 5H).

Preparation of intermediate 3 (R=H)

Product 2 (2.1 g, 4.5 mM) was dissolved in MeOH (220 ml) and $CH_2Cl_2$ (110 ml). A solution of 1N morpholine in MeOH (18 ml, 4 eq.) was added and the solution kept to stand at 40° C. for 5 hr. After neutralization with aqueous N HCl the solvent was removed in vacuo and the residue was crystallized from MeOH to give 3, (1.7 g, yield 90%). m.p. 265° C. (dec.).

IR (KBr): 3440 (phenolic OH), 1745, 1720, 1670 (non-chelated quinone), 1630 (chelated quinone), 1590 $cm^{-1}$.

FD-MS: m/z 436 ($M^{+\cdot}$).

UV and visible spectra (MeOH) λ max: 204, 226, 258, 336, 386, 404 nm.

PMR (200 MHz, $CDCl_3$), inter alia: δ 2.09, 2.04 (s, 6H, $OCOCH_3$), 2.25 (s, 3H, $COCH_3$), 2.54–3.40 (m, 4H), 6.19 (dd, J=3.1, 5.6 Hz, 1H, 7-H), 7.77–8.35 (m, 5H), 13.11 (s, 1H, 11-OH).

(c) Preparation of intermediate 4 (P=H)

To a mixture of 3 (1.6 g, 3.66 mM) +$NH_4NO_3$ (1.6 g, 20 mM)+$(CF_3CO)_2O$ (18 ml) anhydrous $CH_2Cl_2$ (300 ml) was added under nitrogen atmosphere and vigorous stirring at room temperature. After 90' MeOH (3 l) was added: a yellow precipitate was obtained which was filtered, washed with fresh MeOH and ethyl ether. After drying, product 4 (1.23 g, yield 70%) was obtained. m.p. 263°–264° C.

IR (KBr): 3470, 1745, 1720, 1675, 1635, 1585, 1540 (Ar—$NO_2$) $cm^{-1}$.

FD-MS: m/z 481 ($M^{+\cdot}$).

UV and visible spectra (MeOH) λ max: 216, 260, 338, 400 nm.

PMR (200 MHz, $CDCl_3$), inter alia: δ 2.04, 2.00 (s, 6H, $OCOCH_3$), 2.24 (s, 3H, $COCH_3$), 2.43–3.51 (m, 4H), 6.22 (dd, J=2.3, 5.4 Hz, 1H, 7-H), 7.8–8.4 (m, 4H), 13.59 (s, 1H, 11-OH).

(d) Product 4 (1.1 g, 2.3 mM) was dissolved in THF (220 ml). 0.1N NaOH (220 ml) was added at room temperature under nitrogen atmosphere and stirring. After 1 hr the solution was adjusted at pH ca 7 with N HCl and the solvent removed in vacuo. The residue was dissolved with $CH_2Cl_2$, the solution washed with $H_2O$ until neutrality, dried over $Na_2SO_4$ and the solvent evaporated. After a silica gel column chromatography, product 5 (0.77 g, yield 90%) was obtained. m.p. 233°–234° C. (dec.).

IR (KBr): 3570, 3470, 1710, 1680, 1630, 1585, 1535 $cm^{-1}$.

FD-MS: m/z 398 ($MH^+$), 397 ($M^{+\cdot}$).

UV and visible spectra (MeOH) λ max: 216, 260, 341, 384, 401 nm.

PMR (200 MHz, $CDCl_3$), inter alia: δ 2.23–3.22 (m, 4H), 2.41 (s, 3H, $COCH_3$), 4.02 (d, J=8.4 Hz, 1H, 7-OH), 4.67 (s, 1H, 9-OH), 5.02 (ddd, J=2.3, 4.3, 8.4 Hz, 1H, 7-H), 7.8–8.4 (m, 4H), 13.51 (s, 1H-11-OH).

EXAMPLE 2

4-Demethoxy-11-deoxy-11-nitrodaunomycinone 11 (R=H)

(a) Preparation of intermediate 8 (R=H)

Product 7 (0.7 g, 2 mM) was stirred with acetic anhydride (10 ml) and pyridine (10 ml) at room temperature. After 24 hr the reaction mixture was worked-up as described in example 1 (a) to give 8 (0.88 g, yield 93%). m.p. 220°–222° C.

IR (KBr): 1780, 1730, 1720, 1675, 1590 $cm^{-1}$.

UV (MeOH) λ max: 210, 258, 334 nm.

FD-MS: m/z 479 ($MH^+$), 478 ($M^{+\cdot}$).

PMR (200 MHz, $CDCl_3$, T=40° C.), inter alia: δ 2.03 (s, 6H, $OCOCH_3$), 2.23 (s, 3H, $COCH_3$), 2.44 (s, 3H, Ar—$OCOCH_3$), 2.44–3.39 (m, 4H), 6.46 (broad, 1H, 7-H), 7.75–8.3 (m, 5H).

(b) Preparation of intermediate 9 (R=H)

Product 8 (0.83 g, 1.74 mM) was treated in the same manner described in example 1 (b) affording 9 (0.67 g, yield 88%). m.p. 244° C. IR (KBr): 3430, 1730, 1665, 1640, 1590 $cm^{-1}$.

UV and visible spectra (MeOH) λ max: 208, 226, 254, 334, 384, 402 nm.

FD-MS: m/z 436 ($M^{+\cdot}$).

PMR (200 MHz, $CDCl_3$) inter alia: δ 2.04 (s, 6H, $OCOCH_3$), 2.24 (s, 3H, $COCH_3$), 2.40–3.30 (m, 4H), 6.47 (dd, J=2.0, 5.5 Hz, 1H, 7-H), 7.8–8.3 (m, 5H), 13.06 (s, 1H, 6-OH).

(c) Preparation of intermediate 10 (R=H)

Product 9 (0.62 g, 1.42 mM) was treated with $NH_4NO_3$ (0.57 g, 7.1 mM), $(CF_3CO)_2O$ (4 ml) in anhydrous $CH_2Cl_2$ (90 ml). Using the same procedure of example 1 (c) product 10 (0.5 g, yield 73%) was obtained. m.p. 272°–274° C. (dec.).

Ir (KBr): 3450, 1740, 1710, 1680, 1635, 1590, 1545 (Ar—$NO_2$) $cm^{-1}$.

UV and visible spectra (MeOH) λ max: 208, 254, 334, 400 nm.

FD-MS: m/z 481 ($M^{+\cdot}$).

PMR (200 MHz, $CDCl_3$) inter alia: δ 2.06, 2.04 (s, 6H, $OCOCH_3$), 2.2 (s, 3H, $COCH_3$), 2.42–3.03 (m, 4H), 6.50 (dd, J=1.7, 5.5 Hz, 1H, 7-H), 7.8–8.4 (m, 4H), 13.50 (s, 1H, 6-OH).

(d) Product 10 (0.45 g, 0.94 mM) was treated with 0.1N NaOH as described in example 1 (d) giving product 11 (0.34 g, 91% yield). m.p. 231°–233° C. IR(KBr): 3550, 1710, 1675, 1630, 1540 $cm^{-1}$.

UV and visible spectra (MeOH) λ max: 210, 214, 218, 250, 326, 336, 400 nm. FD-MS: m/z 397 ($M^{+\cdot}$).

HRMS Calc. [$C_{20}H_{15}NO_8$]: 397.0798. (Found: 397.0808).

PMR (200 MHz, $CDCl_3$) inter alia: δ 2.18–3.1 (m, 4H), 2.38 (s, 3H, $COCH_3$), 3.85 (d, J=6.2 Hz, 1H, 7-OH), 4.55 (s, 1H, 9-OH), 5.36 (ddd, J=1.8, 4.8, 6.2 Hz, 1H, 7-H), 7.8–8.4 (m, 4H), 13.7 (s, 1H, 6-OH).

EXAMPLE 3

Preparation of 4-demethoxy-6-deoxy-6-nitro-N-trifluoroacetyl-daunorubicin (I)

To a cooled solution (15° C.) of the racemic 4-demethoxy-6-deoxy-6-nitrodaunomycinone 5 (R=H) (0.7 g, 1.76 mM) in anhydrous methylene chloride (140 ml), 1-chloro-N,O-di(trifluoroacetyl) daunosamine (1.88 g, 5.28 mM) (prepared following the procedure on Cancer Chemotherapy Reports Part 3, Vol. 6, No. 2, p. 123) in anhydrous $CH_2Cl_2$ (40 ml) and silver trifluoromethane sulfonate (1.4 g, 5.28 mM) in anhydrous diethyl ether (40 ml) were added simultaneously and rapidly under vigorous stirring and nitrogen bubbling. After 20' saturated aqueous $NaHCO_3$ solution (100 ml) was added and the mixture left to stand under stirring for 10'. The mixture was filtered over celite, the organic layer separated, washed with water, dried over $Na_2SO_4$ and the solvent removed in vacuo. The yellow material was dissolved with MeOH (300 ml) and left to stand overnight at room temperature to remove the O-trifluoroacetyl group. The residue, resulting from the evaporation of the solvent, was chromatographed on silica gel affording α-glycosides 7(S):9(S) (0.43 g, yield 39%) and 7(R):9(R) (0.43 g, yield 39%).

7(S):9(S)

m.p. 245°–246° C.

IR(KBr): 3470, 3450, 1720, 1700 (N-trifluoroacetyl), 1680, 1635, 1590, 1535 $cm^{-1}$.

FD-MS: m/z 623 (MH+).

UV and visible spectra (MeOH) λ max: 208, 260, 341, 384, 401 nm $[\alpha]_D^{25°} = +337$ (c=0.05541 in MeOH).

CD (MeOH): Δε 226 nm=+19.31 , Δε 270 nm=−9.94, Δε 292 nm=+5.67, Δε 340 nm=+7.68.

PMR (200 MHz, $CDCl_3$): δ 1.24 (d, J=6.8 Hz, 3H, 5'—$CH_3$), 1.82 (td, J=4.1, 12.4, 12.4 Hz, 1H, 2'$_{ax}$—H), 1.94 (d, J=8.2 Hz, 1H, 4'—OH), 1.95 (dd, J=5.0, 12.4 Hz, 1H, 2'$_{eq}$—H), 2.15 (dd, J=4.3, 15.1 Hz, 1H, 8$_{ax}$—H), 2.34 (s, 3H, $COCH_3$), 2.48 (ddd, J=1.8, 2.3 15.1 Hz, 1H, 8$_{eq}$—H), 3.10 (d, J=18.7 Hz, 1H, 10$_{ax}$—H), 3.27 (dd, J=1.8, 18.7 Hz, 1H, 10$_{eq}$—H), 3.65 (dd, J=2.7, 8.2 Hz, 1H, 4'—H) 4.1–4.3 (m, 1H, 3'—H), 4.30 (q, J=6.8 Hz, 1H, 5'—H), 5.00 (d, J=4.1 Hz, 1H, 1'—H), 5.11 (dd, J=2.3, 4.3 Hz, 1H, 7-H), 6.61 (d, J=8.0 Hz, 1H, $NHCOCF_3$), 7.8–7.9 (m, 2H, 2-H, 3-H), 8.2–8.4 (m, 2H, 1-H, 4-H), 13.55 (s, 1H, 11-OH).

7(R):9(R)

m.p. 145°–146° C.

FD-MS: m/z 623 (10, MH+); 57 g (100)

CD (MeOH): Δε 226 nm=−10.9, Δε 271 nm=+7.26, Δε 291 nm=−0.27, Δε 300 nm=+0.56, Δε 340 nm=−5.1.

$[\alpha]_D^{25°} = -293$ (c=0.0635 in MeOH).

PMR (200 MHz, $CDCl_3$), inter alia: δ 5.14 (t, J=3.0 Hz, 1H, 7-H), 5.27 (m, 1H, 1'—H).

EXAMPLE 4

Preparation of 4-demethoxy-6-deoxy-6-nitrodaunorubicin hydrochloride (II)

4-demethoxy-6-deoxy-6-nitro-N-trifluoroacetyl-daunorubicin (I) (0.130 g, 0.2 mM) was dissolved in acetone (6 ml). At 0° C., nitrogen atmosphere and stirring 0.1N NaOH (60 ml) was added. After 2 hr the acetone was removed in vacuo and the pH adjusted at 4.5 with 0.1N HCl. The aqueous solution was extracted with $CH_2Cl_2$, adjusted at pH ca 6.5–7.0 with 0.1N NaOH and extracted with $CH_2Cl_2$. The organic layer was washed with $H_2O$, dried over $Na_2SO_4$ and the solvent evaporated. The residue was dissolved with MeOH (5 ml), acidified with some drops of MeOH/HCl solution and the hydrochloride precipitated by addition of diethyl ether and n-hexane. The solid material was filtered, washed with diethyl ether until neutrality and dried to give (II) (0.080 g, yield 68%). m.p. 173° C. (dec.).

IR (KBr): 3400, 1710, 1675, 1630, 1590, 1540 $cm^{-1}$.

FD-MS: m/z 527 (MH+).

EXAMPLE 5

Preparation of 4-demethoxy-11-deoxy-11-nitro-N-trifluoroacetyl · daunorubicin (X)

The racemic aglycone 11 (R=H) (0.290 g, .073 mM) was transformed to the corresponding glycoside as described in example 3. Product X [7(S):9(S)] (0.1 g, yield 24%) and its diastereoisomer [7(R):9(R)] (0.1, yield 24%) were obtained after chromatographic separation.

7(S):9(S)

m.p. 237°–240° C. (dec.).

IR (KBr): 3500, 3400, 1720, 1675, 1640, 1540 $cm^{-1}$.

FD-MS: m/z 570 (M+·—$COCH_3$).

UV and visible spectra (MeOH) λ max: 207, 259, 335, 400 nm.

CD (MeOH): Δε 221 nm=+11.1, Δε 250 nm=+4.0, Δε 289 nm=−5.1, Δε 330 nm=+3.1, Δε 400 nm=+1.0.

$[\alpha]_D^{25°} = +22$ (c=0.0623 in MeOH).

PMR (200 MHz, $CDCl_3$): δ 1.30 (d, J=6.5 Hz, 3H, 5'—$CH_3$), 1.86 (td, J=4.0, 13.0, 13.0 Hz, 1H, 2'$_{ax}$—H), 2.03 (dd, J=4.4, 13.0 Hz, 1H, 2'$_{eq}$—H), 2.13 (dd, J=4.3, 14.9 Hz, 1H, 8$_{ax}$—H), 2.36 (ddd, J=1.6, 2.2, 14.9 Hz, 1H, 8$_{eq}$—H), 2.37 (s, 3H, $COCH_3$), 2.89 (dd, J=1.6, 18.2 Hz, 1H, 10$_{eq}$—H), 3.12 (d, J=18.2 Hz, 1H, 10$_{ax}$—H), 3.68 (dd, J=3.0, 8.0 Hz, 1H, 4'—H), 4.15–4.30 (m, 1H, 3'—H), 4.25 (q, J=6.5 Hz, 1H, 5'—H), 4.30 (s, 1H, 9-OH), 5.30 (dd, J=2.2, 4.3 Hz, 1H, 7-H), 5.47 (d, J=4.5 Hz, 1H, 1'—H), 6.70 (d, J=8.0 Hz, 1H, $NHCOCF_3$), 7.8–7.9 (m, 2H, 2-H, 3-H), 8.2–8.4 (m, 2H, 1-H, 4-H), 13.72 (s, 1H, 6-OH).

7(R):9(R)

FD-MS: m/z 579 (100, M+·—$COCH_3$).

PMR (200 MHz, $CDCl_3$), inter alia: δ 5.35 (m, 1H, 1'—H), 5.59 (dd, J=2.0, 3.5 Hz, 1H, 7-H).

EXAMPLE 6

Preparation of 4-demethoxy-11-deoxy-11-nitrodaunorubicin hydrochloride (XI)

Product X (0.090 g, 0.145 mM) was treated as described in example 4 to give XI (0.061 g, yield 75%). m.p. 212° C. (dec.).

IR (KBr): 3400, 2900, 1710, 1670, 1635, 1590, 1540 $cm^{-1}$.

FD-MS: m/z 527 (MH+).

UV and visible spectra (MeOH) λ max: 208, 222, 256, 402 nm.

EXAMPLE 7

4-Demethoxy-6-deoxy-6-nitrodoxorubicin (III)

Following the technique disclosed in U.S. Pat. No. 3,803,124, the treatment of 4-demethoxy-6-deoxy-6-nitrodaunorubicin, hydrochloride (II) obtained in Example 4, with bromine and then with sodium formate, yielded 4-demethoxy-6-deoxy-6-nitrodoxorubicin (III) which was isolated as the hydrochloride.

EXAMPLE 8

4-Demethoxy-11-deoxy-11-nitrodoxorubicin (XII)

Following the technique disclosed in U.S. Pat. No. 3,803,124, the treatment of 4-demethoxy-11-deoxy-11-nitrodoxorubicin hydrochloride (XI) obtained in Example 6, with bromine and then with sodium formate, yielded 4-demethoxy-11-deoxy-11-nitrodoxorubicin (XII) which was isolated as the hydrochloride.

The invention also provides pharmaceutical compositions comprising an anthracycline glycoside of formula (A') or a pharmaceutically acceptable salt thereof in admixture with a pharmaceutically acceptable diluent or carrier. A therapeutically effective amount of a compound of formula (A') or salt thereof may be combined with an inert carrier or diluent.

The compounds of formula (A') and their salts are useful in methods of treatment of the human or animal, that is mammalian, body by therapy. They are useful as anti-tumor agents by administering a therapeutically effective amount to a patient. They may be used in a method of treatment of the human or animal body by surgery or therapy or of diagnosis practiced on the human or animal body.

Biological activity of Compound XI and Compound II

The compounds have been teated in comparison with daunorubicin (DNR) against HeLa and P388 cells in vitro. The compounds were tested by dissolving them, as hydrochlorides, in water.

The in vivo effect of Compound XI against P 388 ascitic leukemia is reported in Table 1.

The activity of Compounds XI and II was tested against disseminated Gross leukemia. The results are reported in Table 2. In this system the two new compounds at the maximal tested dose (22.5 mg/Kg of XI, 50 mg/Kg of II) were more active than DNR at the maximal tolerated dose (10 mg/Kg).

TABLE 1

| Effect against P388 ascitic leukemia[a] | | | |
|---|---|---|---|
| Compound | dose[b] | T/C %[c] | Toxic[d] death |
| DNR | 2.9 | 152 | 1/10 |
| | 4.4 | 157 | 5/10 |
| Compound XI | 4 | 152 | 0/10 |
| | 6 | 162 | 0/10 |
| | 9 | 171 | 1/10 |
| | 13.5 | 124 | 9/10 |

[a]Experiments were performed in CDF$_1$ mice, inoculated with 10$^6$ leukemia cells i.p.
[b]Treatment i.p. on day 1 after tumor inoculum.
[c]Median survival time of treated mice/median survival time of control × 100.
[d]Evaluated on the basis of autoptic findings.

TABLE 2

| Effect against Gross leukemia[a] | | | |
|---|---|---|---|
| Compound | dose[b] mg/kg | T/C % | Toxic[d] deaths |
| DNR | 10 | 158,150 | 0/20 |
| | 15 | 175,225 | 3/20 |
| Compound XI | 10 | 125 | 0/10 |
| | 15 | 150 | 0/10 |
| | 22.5 | 200 | 0/10 |
| Compound II | 25 | 175 | 0/10 |
| | 50 | 208 | 0/10 |

[a]Experiments were performed in C3H mice, inoculated with 2 × 10$^6$ leukemia cells i.v.
[b]Treatment i.v. on day 1 after tumor inoculum.
[c]Median survival time of treated mice/median survival time of controls × 100.
[d]Evaluated on the basis of autoptic findings.

We claim:

1. An anthracycline glycoside of the formula (A'):

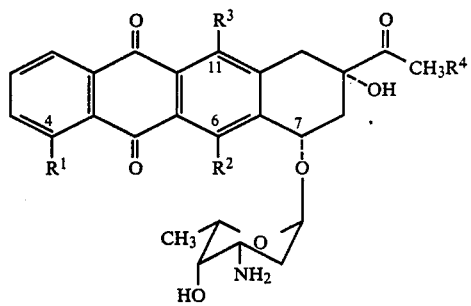

wherein $R^1$ represents a hydrogen atom, a hydroxy group or a methoxy group; one of $R^2$ and $R^3$ represents a hydroxy group and the other of $R^2$ and $R^3$ represents a nitro group; and $R^4$ represents a hydrogen atom or a hydroxy group; and pharmaceutically acceptable salts thereof.

2. A compound according to claim 1, which is in the form of a hydrochloride salt.

3. A compound according to claim 1, which is 4-demethoxy-6-deoxy-6-nitrodaunorubicin hydrochloride.

4. A compound according to claim 1, which is 4-demethoxy-11-deoxy-11-nitrodaunorubicin hydrochloride.

5. A compound according to claim 1, which is 4-demethoxy-6-deoxy-6-nitrodoxorubicin hydrochloride.

6. A compound according to claim 1, which is 4-demethoxy-11-deoxy-11-nitrodoxorubicin hydrochloride.

7. A compound of formula (A'''):

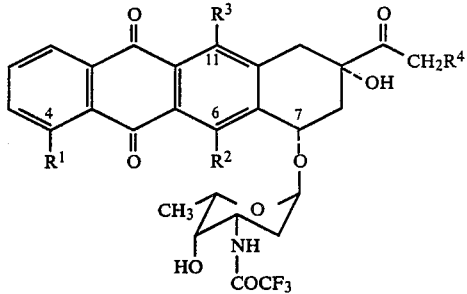

wherein $R^1$ represents a hydrogen atom, a hydroxy group or a methoxy group; one of $R^2$ and $R^3$ represents a hydroxy group and the other of $R^2$ and $R^3$ represents a nitro group; and Rhu 4 represents a hydrogen atom or a hydroxy group.

8. An aglycone of formula (B)

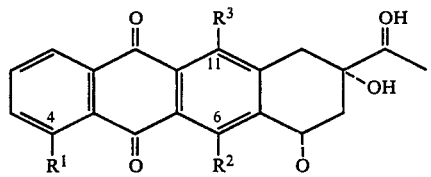

wherein $R^1$ represents a hydrogen atom, a hydroxy group or a methoxy group; and one of $R^2$ and $R^3$ represents a hydroxy group and the other of $R^2$ and $R^3$ represents a nitro group.

9. A compound according to claim 8, which is (±) 4-demethoxy-6-deoxy-6-nitrodaunomycinone.

10. A compound according to claim 8, which is (±) 4-demethoxy-11-deoxy-11-nitrodaunomycinone.

11. A process for the preparation of an aglycone according to claim 8 in which R' is hydrogen or methoxy which process comprises selectively protecting the C-7 and C-9 hydroxy groups of (±) 4-demethoxy-6-deoxydaunomycinone, (±) 6-deoxydaunomycinone, (±) 4-demethoxy-11-deoxydaunomycinone or 11-deoxydaunomycinone; nitrating the ring B of the compound thus-formed at the para-position with respect of hydroxy substituent on ring B; and removing the C-7 and C-9 hydroxy protecting groups so as to obtain an aglycone of formula (B) in which $R^1$ is hydrogen or methoxy: by the sequential steps of reacting (±) 4-demethoxy-6-deoxydaunomycinone, (±) 6-deoxydaunomycinone, (±) 4-demethoxy-11-deoxydaunomycinone or 11-deoxydaunomycinone with acetic anhydride and pyridine at from 85° to 90° C. to acrylate all the free hydroxy groups; selectively hydrolyzing the so formed triacetate by 1N morpholine in methanol at 40° C. for 5 hours so as to obtain the C—7—OH and C-9—OH diacetate; treating the diacetate at room temperature, under a nitrogen atmosphere and with vigorous stirring with an excess of trifluoroacetic anhydride/ammonium nitrate in methylene chloride to afford the corresponding 6- or 11-nitro derivative; removing the 7- and 9-acetyl protecting groups from the said derivative by hydrolysis in tetrahydrofurane with 0.1N sodium hydroxide, at room temperature under nitrogen atmosphere so as to obtain the desired 6- or 11-nitro aglycone of formula (B) in which $R^1$ is hydrogen or a methoxy group.

12. A process according to claim 11, in which the 6- or 11-nitro aglycone of formula (B) wherein $R^1$ is a methoxy group is subjected to a mild 4-dealkylation by means of $AlCl_3$ in nitrobenzene so as to obtain the 6- or 11-nitro aglycone of formula (B) in which $R^1$ is a hydroxy group.

13. A process according to claim 11 in which the aglycone product of the process of claim 11 is purified by chromotography on silica gel.

14. A pharmaceutical composition for treating P388 ascitic leukemia in a host afflicted therewith comprising an amount effective for treating said leukemia of an anthracycline glycoside according to claim 1 or a pharmaceutically acceptable salt thereof in admixture with a pharmaceutically acceptable diluent or carrier.

15. A method of treating P388 ascitic leukemia in a host afflicted therewith which comprises administering to the host an amount effective for treatment of said leukemia of an anthracycline glycoside according to claim 1 or a pharmaceutically acceptable salt thereof.

* * * * *